(12) United States Patent
Tassoni, Jr. et al.

(10) Patent No.: US 9,717,882 B2
(45) Date of Patent: Aug. 1, 2017

(54) MULTI-LUMEN CATHETERS AND RELATED METHODS OF MANUFACTURE

(71) Applicant: BOSTON SCIENTIFIC SCIMED, INC., Maple Grove, MN (US)

(72) Inventors: Anthony F. Tassoni, Jr., Ramsey, MN (US); Martin R. Willard, Burnsville, MN (US); Patrick A. Haverkost, Brooklyn Center, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 366 days.

(21) Appl. No.: 14/613,177

(22) Filed: Feb. 3, 2015

(65) Prior Publication Data

US 2015/0217084 A1 Aug. 6, 2015

Related U.S. Application Data

(60) Provisional application No. 61/936,167, filed on Feb. 5, 2014.

(51) Int. Cl.
*A61M 25/00* (2006.01)
*A61L 29/04* (2006.01)
(Continued)

(52) U.S. Cl.
CPC ......... *A61M 25/0009* (2013.01); *A61L 29/04* (2013.01); *A61L 29/14* (2013.01);
(Continued)

(58) Field of Classification Search
CPC .......... A61M 25/0009; A61M 25/0012; A61M 25/0026; A61M 25/0034; A61M 25/0037; A61M 25/005; A61M 2025/0031; A61M 2025/0034; A61M 2025/0037; A61M 2025/0046; A61M 2025/0183; A61M 2025/0188; A61L 29/04; A61L 29/14;
(Continued)

(56) References Cited

U.S. PATENT DOCUMENTS

| 399,985 A | 3/1889 | Goodwillie |
| 1,696,018 A | 12/1928 | Schellberg |

(Continued)

FOREIGN PATENT DOCUMENTS

| WO | 03063941 A1 | 8/2003 |
| WO | 2007053741 A1 | 5/2007 |

*Primary Examiner* — Christopher M Koehler
(74) *Attorney, Agent, or Firm* — Seager, Tufte & Wickhem, LLP

(57) ABSTRACT

A method of making a multi-lumen catheter may include disposing an outer surface of a mandrel against an outer surface of a first catheter; disposing a first heat shrink material around the first catheter and the mandrel; heating the first catheter and the mandrel to form a U-shaped channel along the outer surface of the first catheter; removing the first heat shrink material and the mandrel from the first catheter; placing a second catheter into the U-shaped channel; disposing a second heat shrink material around the first catheter and the second catheter such that the second catheter is retained within the U-shaped channel; and heating the first catheter and the second catheter to cause reflow between the first catheter and the second catheter to form the multi-lumen catheter.

20 Claims, 14 Drawing Sheets

(51) Int. Cl.
*A61L 29/14* (2006.01)
*A61M 25/01* (2006.01)

(52) U.S. Cl.
CPC ....... *A61M 25/0026* (2013.01); *A61M 25/005* (2013.01); *A61M 2025/0031* (2013.01); *A61M 2025/0034* (2013.01); *A61M 2025/0037* (2013.01); *A61M 2025/0046* (2013.01); *A61M 2025/0183* (2013.01); *A61M 2025/0188* (2013.01); *Y10T 29/49826* (2015.01)

(58) Field of Classification Search
CPC ......... Y10T 29/49826; Y10T 29/49805; Y10T 29/53652; B29C 2043/028
See application file for complete search history.

(56) References Cited

U.S. PATENT DOCUMENTS

| | | | |
|---|---|---|---|
| 2,173,527 A | 9/1937 | Agayoff | |
| 2,561,569 A | 7/1951 | Flynn | |
| 3,064,653 A | 11/1962 | Coanda | |
| 3,174,890 A | 3/1965 | Goyke | |
| 3,322,590 A | 5/1967 | Clark | |
| 3,467,180 A | 9/1969 | Pensotti | |
| 3,469,579 A | 9/1969 | Hubert | |
| 3,625,793 A | 12/1971 | Sheridan | |
| 3,720,210 A | 3/1973 | Diettrich | |
| 3,817,389 A | 6/1974 | Weichselbaum | |
| 3,976,529 A | 8/1976 | Weichselbaum | |
| 4,003,665 A | 1/1977 | Dreyer | |
| 4,050,667 A | 9/1977 | Kossett | |
| 4,063,980 A | 12/1977 | Trunnell | |
| 4,072,146 A | 2/1978 | Howes | |
| 4,838,881 A | 6/1989 | Bennett | |
| 5,042,985 A | 8/1991 | Elliott | |
| 5,167,623 A * | 12/1992 | Cianci | A61M 25/0026 604/43 |
| 5,221,256 A | 6/1993 | Mahurkar | |
| 5,295,962 A | 3/1994 | Crocker | |
| 5,300,099 A | 4/1994 | Rudie | |
| 5,322,508 A | 6/1994 | Viera | |
| 5,342,301 A | 8/1994 | Saab | |
| 5,569,184 A | 10/1996 | Crocker | |
| 5,571,086 A | 11/1996 | Kaplan | |
| 5,624,392 A * | 4/1997 | Saab | A61F 7/123 604/113 |
| 6,013,190 A | 1/2000 | Berg et al. | |
| 6,102,904 A | 8/2000 | Vigil | |
| 6,306,074 B1 | 10/2001 | Waksman | |
| 6,524,302 B2 | 2/2003 | Kelley | |
| 7,276,043 B2 | 10/2007 | Heath et al. | |
| 8,430,837 B2 | 4/2013 | Jenson et al. | |
| 8,751,018 B1 * | 6/2014 | Sethna | A61N 1/05 607/119 |
| 2006/0161100 A1 * | 7/2006 | Hamboly | A61M 25/0009 604/43 |
| 2007/0005003 A1 * | 1/2007 | Patterson | A61M 25/0012 604/43 |
| 2007/0010847 A1 * | 1/2007 | Pepper | A61M 25/0014 606/194 |
| 2007/0016133 A1 * | 1/2007 | Pepper | A61M 25/0052 604/103.04 |
| 2007/0106211 A1 * | 5/2007 | Provost-Tine | A61M 25/0009 604/96.01 |
| 2009/0204052 A1 * | 8/2009 | Nimkar | A61M 25/001 604/6.16 |
| 2009/0287166 A1 * | 11/2009 | Dang | A61M 25/00 604/265 |
| 2011/0144581 A1 * | 6/2011 | Irwin | A61M 25/0009 604/103 |
| 2012/0150107 A1 | 6/2012 | Cheung et al. | |
| 2013/0123752 A1 * | 5/2013 | Pursley | A61M 25/0009 604/528 |
| 2015/0306805 A1 * | 10/2015 | Dando | B29C 47/0026 264/515 |
| 2016/0114130 A1 * | 4/2016 | Brown | A61M 25/001 604/529 |

* cited by examiner

MULTI-LUMEN CATHETERS AND RELATED METHODS OF MANUFACTURE

CROSS-REFERENCE TO RELATED APPLICATIONS

This application claims priority under 35 U.S.C. §119(e) to U.S. Provisional Application No. 61/936,167, filed Feb. 5, 2014, the entire disclosure of which is herein incorporated by reference.

FIELD

The disclosure is generally directed to medical devices and related methods of manufacture. In particular, the disclosure is directed toward multi-lumen catheters and related methods of manufacture.

BACKGROUND

Certain medical procedures, such as thrombectomy, angioplasty, and so on, require a catheter that is navigated through a patient's vasculature to a target site for treatment. The catheter has to have sufficient flexibility and column strength so that it may be torqued, pushed, and pulled on its way through the vascular passages to the target site within the patient's body. It is also preferable for the catheter to have a relatively small profile so that it can access narrow vasculature with minimal damage to surrounding tissue. In addition, a relatively small profile may be preferred so as to minimize the amount of polymer materials needed to manufacture the catheter.

In some cases, catheters with multiple lumens (also referred to as "multi-lumen catheters") may be needed to allow fluid communication with the target site, and/or to allow another medical device such as a stent or balloon, for example, to access the target site. For some procedures, such as thrombectomy, a separate guidewire lumen may be desirable to guide the catheter to the target site, while the main lumen may be used for aspiration to remove blood clots and/or other debris from the target site.

In an example process, a multi-lumen catheter may be fabricated by joining two or more tubular members together, each having a wall thickness around its lumen. Joining the walls of the two tubular members increases the overall diameter of the multi-lumen catheter, thereby reducing the flexibility of the multi-lumen catheter.

One approach to reduce the profile of a multi-lumen catheter is to reduce the wall thickness of the tubes that are combined in fabricating the multi-lumen catheter. However, such fabrication of a thinner-walled multi-lumen catheter may not have sufficient column strength to easily navigate through tortuous vascular passages. For example, kinks may develop during navigation and/or one or more lumens of the catheter may collapse under external fluid pressure and/or internal vacuum created during aspiration.

Therefore, there is a need for an improved multi-lumen catheter that has a smaller profile with sufficient flexibility and column strength for easy navigation and adequate resistance to radial collapse.

SUMMARY

A method of making a multi-lumen catheter may include obtaining a first polymeric catheter having a first outer surface and a first lumen having a first inner diameter extending longitudinally therethrough along a first central axis; aligning an elongate mandrel having an outer surface and a central axis extending longitudinally therethrough side-by-side with the first polymeric catheter such that the first outer surface contacts the outer surface of the elongate mandrel, and the first central axis may be parallel to the central axis of the elongate mandrel; constricting a first heat shrink material around the first polymeric catheter and the elongate mandrel; heating the first polymeric catheter and the elongate mandrel while bound by the first heat shrink material and urging the first polymeric catheter and the elongate mandrel toward each other along a plane extending between the first central axis and the central axis of the elongate mandrel to form a U-shaped channel along the first outer surface; cooling the first polymeric catheter and the elongate mandrel while bound by the first heat shrink material; removing the first heat shrink material and the elongate mandrel from the first polymeric catheter; placing a second polymeric catheter having a second outer surface and a second lumen having a second inner diameter smaller than the first inner diameter extending longitudinally therethrough along a second central axis into the U-shaped channel such that the second outer surface may be placed into contact with the first polymeric catheter; constricting a second heat shrink material around the first polymeric catheter and the second polymeric catheter such that the second polymeric catheter may be retained within the U-shaped channel; heating the first polymeric catheter and the second polymeric catheter while bound by the second heat shrink material to cause reflow between the first polymeric catheter and the second polymeric catheter to form the multi-lumen catheter; cooling the first polymeric catheter and the second polymeric catheter while bound by the second heat shrink material; and removing the second heat shrink material from the multi-lumen catheter.

A method of making a multi-lumen catheter may include obtaining a first thermoplastic catheter having a first outer surface and a first lumen having a first inner diameter extending longitudinally therethrough along a first central axis; aligning an elongate mandrel having an outer surface and a central axis extending longitudinally therethrough side-by-side with the first thermoplastic catheter such that the first outer surface contacts the outer surface of the elongate mandrel, and the first central axis may be parallel to the central axis of the elongate mandrel; constricting a first heat shrink material around the first thermoplastic catheter and the elongate mandrel; heating the first thermoplastic catheter and the elongate mandrel while bound by the first heat shrink material and urging the first thermoplastic catheter and the elongate mandrel toward each other along a plane extending between the first central axis and the central axis of the elongate mandrel to form a U-shaped channel along the first outer surface; cooling the first thermoplastic catheter and the elongate mandrel while bound by the first heat shrink material; removing the first heat shrink material and the elongate mandrel from the first thermoplastic catheter; placing a second thermoset catheter having a second outer surface and a second lumen having a second inner diameter smaller than the first inner diameter extending longitudinally therethrough along a second central axis into the U-shaped channel such that the second outer surface may be placed into contact with the first thermoplastic catheter; constricting a second heat shrink material around the first thermoplastic catheter and the second thermoset catheter such that the second thermoset catheter may be retained within the U-shaped channel; heating the first thermoplastic catheter and the second thermoset catheter while bound by the second heat shrink material to cause the first thermoplastic catheter to reflow around and encapsulate the second thermoset catheter to form the multi-lumen catheter; cooling the first thermoplastic catheter and the second thermoset catheter while bound by the second heat shrink material; and removing the second heat shrink material from the multi-lumen catheter.

A multi-lumen catheter may include a first polymeric catheter having a first lumen extending therethrough, a first outer surface, and a U-shaped channel formed into the first outer surface; and a second polymeric catheter having a second lumen smaller than the first lumen extending therethrough, the second polymeric catheter being disposed within the U-shaped channel; wherein the second polymeric catheter may be fused to the first polymeric catheter using a reflow process.

A multi-lumen catheter may include a first polymeric catheter having a first lumen extending therethrough, a first outer surface, and a U-shaped channel formed into the first outer surface; and a second polymeric catheter having a second lumen smaller than the first lumen extending therethrough, the second polymeric catheter being disposed within the U-shaped channel; wherein the second polymeric catheter may be mechanically interlocked to the first polymeric catheter using a reflow process.

A method of making a multi-lumen catheter may include obtaining a first polymeric catheter having a first outer surface and a first lumen extending longitudinally therethrough; disposing an outer surface of an elongate mandrel against the first outer surface; disposing a first heat shrink material around the first polymeric catheter and the elongate mandrel; heating the first polymeric catheter and the elongate mandrel to form a U-shaped channel along the first outer surface; removing the first heat shrink material and the elongate mandrel from the first polymeric catheter; placing a second polymeric catheter having a second outer surface and a second lumen extending longitudinally therethrough into the U-shaped channel such that the second outer surface is placed into contact with the first polymeric catheter; disposing a second heat shrink material around the first polymeric catheter and the second polymeric catheter such that the second polymeric catheter is retained within the U-shaped channel; heating the first polymeric catheter and the second polymeric catheter to cause reflow between the first polymeric catheter and the second polymeric catheter to form the multi-lumen catheter; and removing the second heat shrink material from the multi-lumen catheter.

Figure 1:
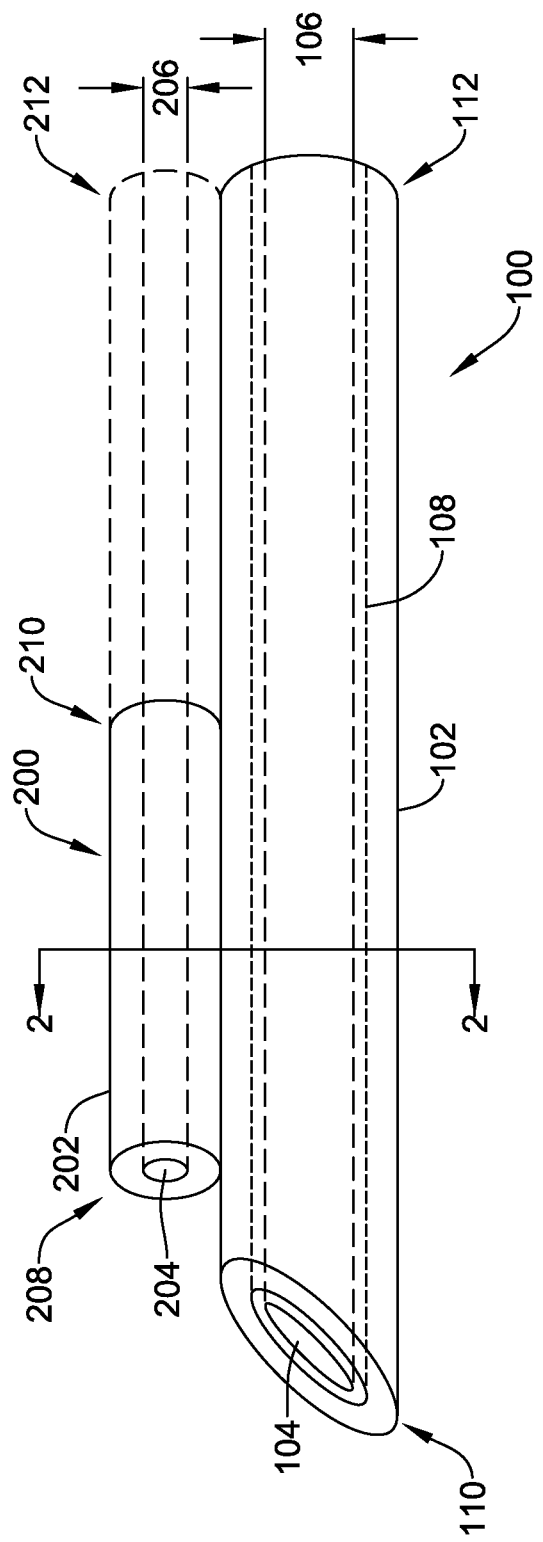
FIGS. 1-4 illustrate aspects of a conventional method of manufacturing a multi-lumen catheter.

While embodiments of the present disclosure are amenable to various modifications and alternative forms, specifics thereof have been shown by way of example in the drawings, which are not necessarily to scale, and will be described in greater detail below. It should be understood, however, that the intention is not to limit aspects of the disclosure to the particular embodiments described. On the contrary, the intention is to cover all modifications, equivalents, and alternatives falling within the spirit and scope of the present disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Turning to FIGS. 1-4, an example method of manufacturing a multi-lumen catheter is schematically depicted. FIG. 1 illustrates a first catheter 100 and a second catheter 200, which may be joined to form a multi-lumen catheter. The first catheter 100 may include a first outer surface 102 and a first lumen 104 having a first inner diameter 106. The first lumen 104 may be a central bore within the first catheter 100 and may extend longitudinally along a first central axis of the first catheter 100 from a proximal end 112 to a distal end 110. In at least some embodiments, the distal end 110 may be skived, angled, or otherwise slanted. In some embodiments, the first catheter 100 may have a mandrel disposed within the first lumen 104 to maintain the first inner diameter 106 during subsequent heating and/or reflow operations.

The first catheter 100 may further include a reinforcing braid 108 embedded between the first lumen 104 and the first outer surface 102. For example, the reinforcing braid 108 may be disposed within the wall of the first catheter 100. The reinforcing braid 108 may be a mesh-like structure that surrounds the first lumen 104.

The second catheter 200 may include a second outer surface 202 and a second lumen 204 having a second inner diameter 206. In some cases, the second inner diameter 206 may be less than the first inner diameter 106. The second lumen 204 may be located within the second outer surface 202 and extend longitudinally therethrough along a second central axis of the second catheter 200. In some embodiments, the second catheter 200 may have a mandrel disposed within the second lumen 204 to maintain the second inner diameter 206 during subsequent heating and/or reflow operations.

The second catheter 200 may be placed side-by-side with the first catheter 100 so that the first central axis is substantially parallel to the second central axis. The second catheter 200 may be longitudinally disposed over the first catheter 100 such that the first outer surface 102 may contact the second outer surface 202.

The second catheter 200 may have a distal end 208 located proximal of and/or adjacent to a distal end 110 of the first catheter 100. In embodiments where the length of the first catheter 100 and the second catheter 200 are the same or similar, a first proximal end 212 of the second catheter 200 may be located over a proximal portion of the first catheter 100 adjacent the proximal end 112. In embodiments where the second catheter 200 is substantially shorter than the first catheter 100, an alternative, second proximal end 210 of the shortened-length second catheter 200 may be disposed distal of the proximal end the first catheter 100. For example, the second proximal end 210 of the second catheter 200 may be located over a distal portion of the first catheter 100. The first catheter 100 and the second catheter 200 may be made up of one or more biocompatible thermoplastic polymers.

Figure 2:
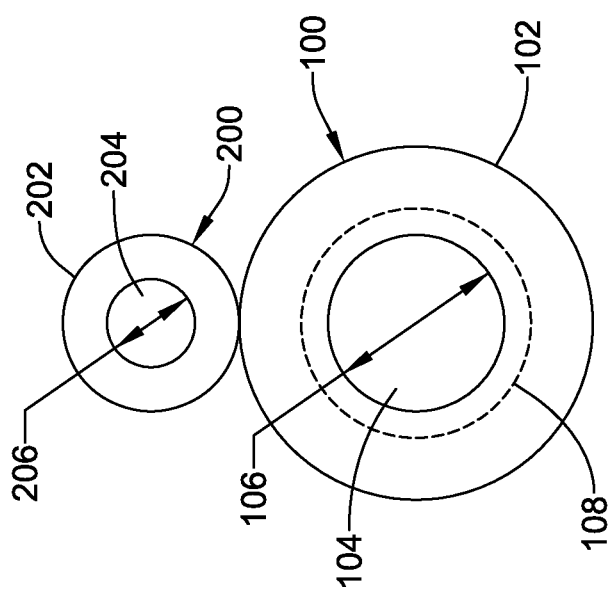

FIG. 2 illustrates a cross-sectional view of the first catheter 100 and second catheter 200 as seen along the plane 2-2 of FIG. 1. The second catheter 200 may be disposed over the first catheter 100 to have a separation between the first lumen 104 and the second lumen 204. The separation may be defined as the sum of a first wall thickness of the first catheter 100 and a second wall thickness of the second catheter 200. The first wall thickness may be defined as a thickness extending between the first outer surface 102 and the first lumen 104. The second wall thickness may be defined as a thickness extending between the second outer surface 202 and the second lumen 204.

Figure 3:
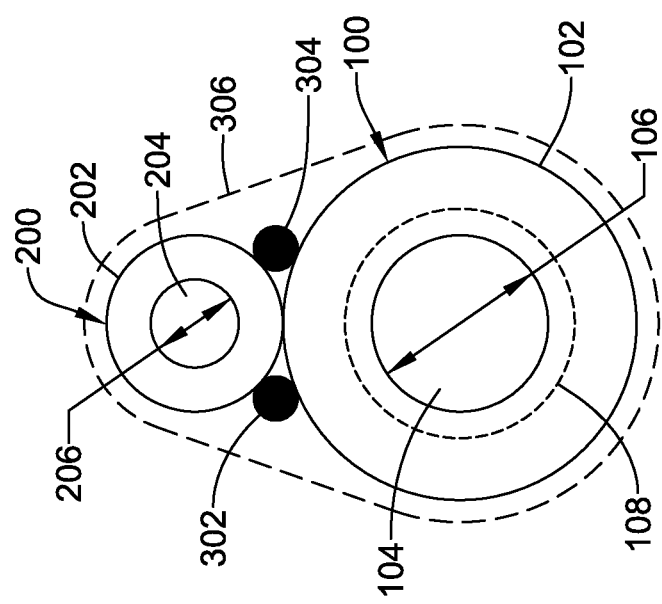

In some embodiments, additional polymeric material may be needed during the manufacture of a multi-lumen catheter. As shown in FIG. 3 for example, a first bead stock element 302 and a second bead stock element 304 may be placed on opposing sides of a plane extending through the first central axis and the second central axis. The first bead stock element 302 and the second bead stock element 304 may be formed of a polymeric material that is compatible with the first catheter 100 and the second catheter 200. The first bead stock element 302 and the second bead stock element 304 may be placed in contact with both the first catheter 100 and the second catheter 200. The first bead stock element 302 and the second bead stock element 304 may be constricted against the first catheter 100 and the second catheter 200 using a heat shrink material 306. The first catheter 100, the second catheter 200, the first bead stock element 302, and the second bead stock element 304 may be heated while bound by the heat shrink material 306 using a suitable tool such as a tube oven, a hot air nozzle, or the like. The heat may cause the polymeric materials of the first catheter 100, the second catheter 200, the first bead stock element 302, and the second bead stock element 304 to melt together. As mentioned previously, the mandrel(s) disposed within the first lumen 104 and/or the second lumen 204 may maintain the first inner diameter 106 and/or the second inner diameter 206, respectively.

Figure 4:
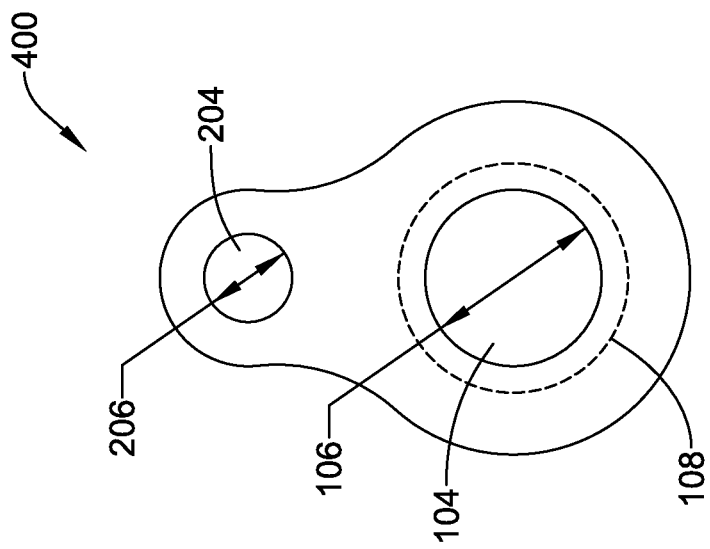

Subsequently, the first catheter 100, the second catheter 200, the first bead stock element 302, and the second bead stock element 304 may be cooled while being bound by the heat shrink material 306 to form the multi-lumen catheter 400 illustrated in cross-section in FIG. 4, which illustrates the multi-lumen catheter 400 after the heat shrink material 306 has been removed.

Figure 5:
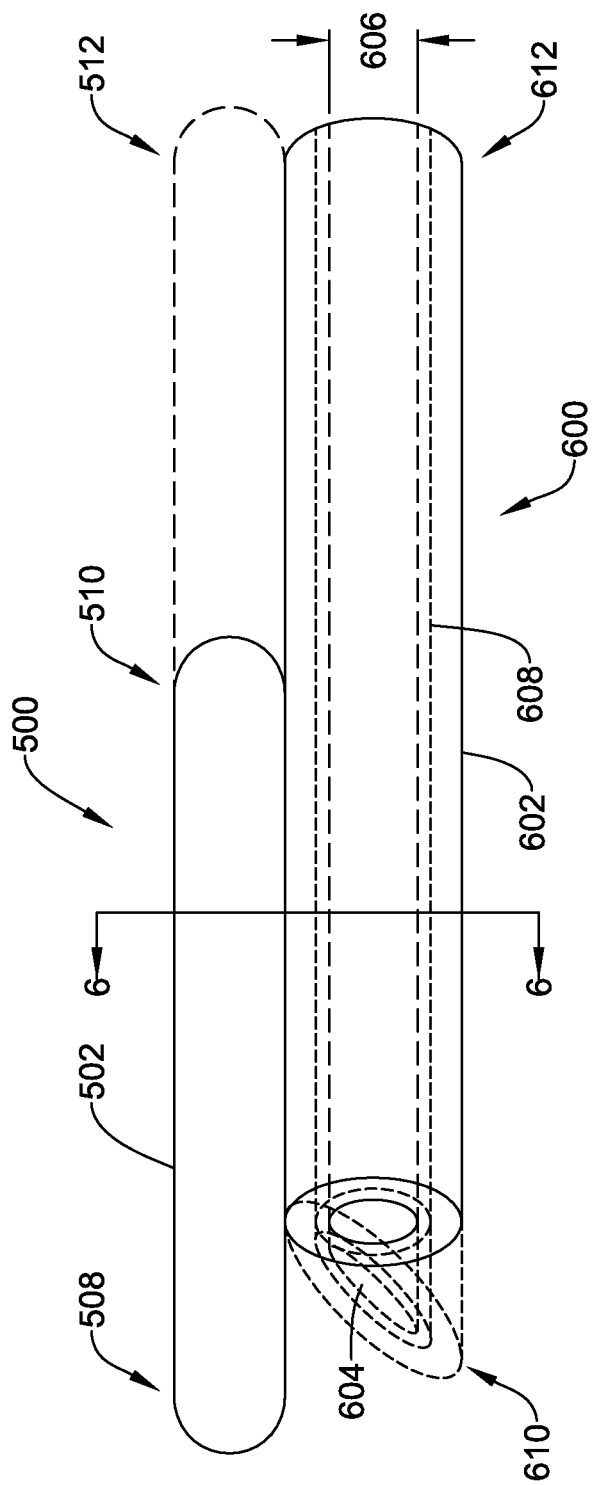
FIGS. 5-13 illustrate aspects of a method of manufacturing a multi-lumen catheter with a reduced profile.

An example method of manufacturing a multi-lumen catheter having a reduced profile is shown illustratively in FIGS. 5-13. FIG. 5 illustrates a first catheter 600 in contact with an elongate mandrel 500 for manufacturing a multi-lumen catheter. In some embodiments, the first catheter 600 may include a first lumen 604, a first outer surface 602, a reinforcing braid or coil 608, a distal end 610, and a proximal end 612. In at least some embodiments, the distal end 610 may be skived, angled, or otherwise slanted relative to a longitudinal axis of the first catheter 600, as shown for example, in FIG. 5 in phantom. In some embodiments, the distal end 610 may be arranged at a non-perpendicular angle and/or a non-parallel angle relative to the longitudinal axis of the first catheter 600. In some embodiments, the distal end 610 may be arranged at an angle of about 1 degree to about 89 degrees, about 20 degrees to about 70 degrees, about 30 degrees to about 60 degrees, about 40 degrees to about 50 degrees, or about 45 degrees relative to the longitudinal axis of the first catheter 600. Other atraumatic distal tip constructions are also contemplated.

In some embodiments, the reinforcing braid or coil 608 may be disposed and/or embedded within a wall of the first catheter 600 extending from the first lumen 604 to the first outer surface 602 to define a first wall thickness. In some embodiments, the reinforcing braid or coil 608 may be a mesh-like structure and/or may include, but is not limited to, an axial or a biaxial reinforcing braid with a suitable reinforcing braid pitch angle. Other reinforcing braid configurations are also contemplated. In some embodiments, the reinforcing braid or coil 608 may be a helical coil structure having a suitable coil pitch or spacing between adjacent loops of the coil. In some embodiments, the first lumen 604 may be formed as a central bore having a first inner diameter 606 and extending longitudinally along a first central axis from the proximal end 612 to the distal end 610. In some embodiments, the first catheter 600 may include and/or be formed of a suitable biocompatible polymeric material. Some suitable polymeric materials may be listed below. In some embodiments, the first lumen 604 may include and/or be coated with a suitable friction-reducing material.

In some embodiments, the first catheter 600 may include a first mandrel disposed within the first lumen 604 to maintain the first inner diameter 606 during subsequent heating and/or reflow operations. In some embodiments, the first mandrel may be formed from a highly polished metallic material, and an etched PTFE liner may be disposed over the first mandrel. During subsequent heating and/or reflow operations, the PTFE liner may be joined or attached to the polymeric material of the first catheter 600 to thereby form a wall of the first lumen 604. Following the subsequent heating and/or reflow operations, the first mandrel may be removed from the first lumen 604 using various suitable methods known in the art, with the PTFE liner remaining within the first catheter 600. In some embodiments, the first mandrel may include, may be formed of, or may be coated with a lubricious and/or "non-stick" coating, such as PTFE or other suitable coatings, which may permit easier extraction of the first mandrel from the first lumen 604 of the first catheter 600. Following the subsequent heating and/or reflow operations, the first mandrel may be removed from the first lumen 604 using various suitable methods known in the art. In some embodiments, the first mandrel (with or without a coating) and/or the etched PTFE liner may further include or be coated with a release agent.

In some embodiments, the first catheter 100 may be longitudinally aligned side-by-side with an elongate mandrel 500 having an outer surface 502 and a central axis extending through the elongate mandrel 500 from a distal end 508 to a first proximal end 512 and/or a second proximal end 510. In some embodiments, the elongate mandrel 500 may extend proximally from the distal end 610 of the first catheter 600 to a second proximal end 510 disposed adjacent a distal portion of the first catheter 600. In some embodiments, the elongate mandrel 500 may extend proximally from the distal end 610 of the first catheter 600 to a different location along the first catheter 600. For example, as shown by the dashed line in FIG. 5, in some embodiments, the elongate mandrel 500 may extend proximally to a first proximal end 512 disposed adjacent to or extending proximal of a proximal end 612 of the first catheter 600. In some embodiments, the outer surface 502 of the elongate mandrel 500 may be in contact with the first outer surface 602 of the first catheter 600 and the central axis of the elongate mandrel 500 may be substantially parallel to the first central axis of the first catheter 600. The elongate mandrel 500 may include, may be formed of, or may be coated with a suitable friction-reducing material. In some embodiments, the elongate mandrel 500 may further include or be coated with a release agent.

Figure 6:
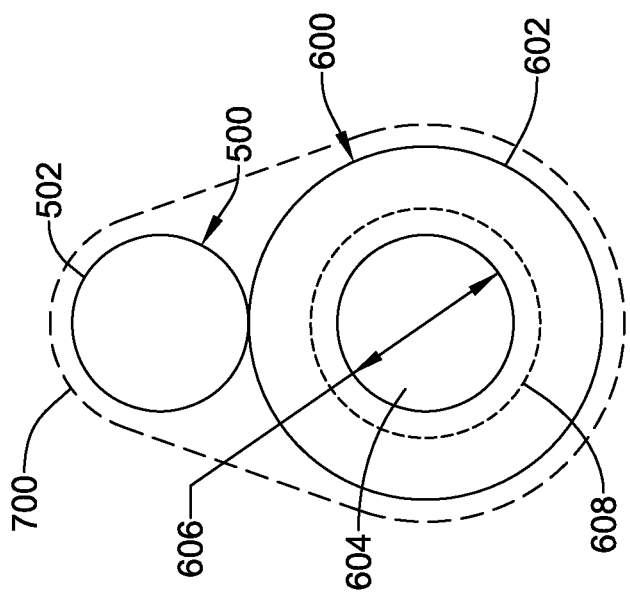
Figure 7:
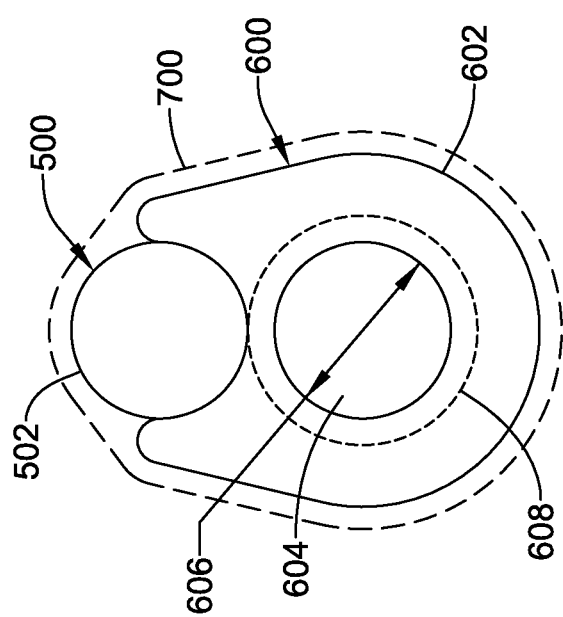
Figure 8:
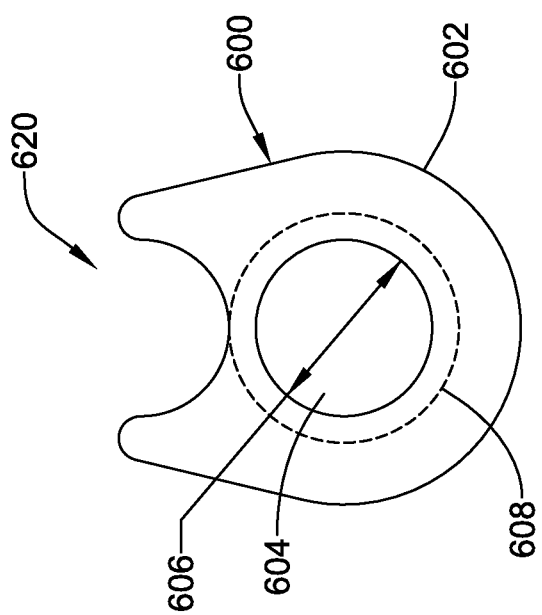

FIG. 6 illustrates a cross-sectional view of the first catheter 600 and the elongate mandrel 500 of FIG. 5 as seen along the plane 6-6. In some embodiments, the first catheter 600 and the elongate mandrel 500 may be constricted with a first heat shrink material 700. In some embodiments, the first heat shrink material 700 may be a flexible jacket or tubing that may be disposed over the first catheter 600 and the elongate mandrel 500 and then heated to constrict the first heat shrink material 700 around and/or onto the first catheter 600 and the elongate mandrel 500, thereby coupling the first catheter 600 and the elongate mandrel 500 together. In some embodiments, the first heat shrink material 700 may be chosen from a variety of heat shrink materials known in the art. In some embodiments, the first heat shrink material 700 may have a designed shrink ratio and wall thickness configured to shrink to a recovered inner diameter or extent when heated. In some embodiments, the recovered inner diameter or extent may be less than a target outer diameter or extent of the first catheter 600 and the elongate mandrel 500 combined so as to create/apply inward force to the reflowing material(s). The wall thickness and/or the differential between the target outer diameter extent and the smaller recovered inner diameter or extent may be used/designed to control and/or generate the desired inward force (i.e., urging).

In some embodiments, the first catheter 600 (with the first mandrel disposed within the first lumen 604) and the elongate mandrel 500 may be heated while being bound by the first heat shrink material 700. In some embodiments, the first catheter 600 and the elongate mandrel 500 may be urged toward each other along a plane extending between the first central axis of the first catheter 600 and the central axis of the elongate mandrel 500 during heating, as illustrated in cross-section in FIG. 7. In some embodiments, while the elongate mandrel 500 is being urged toward the first catheter 600, the elongate mandrel 500 may displace polymeric material from the first outer surface 602 outward within the first heat shrink material 700 to form a U-shaped channel 620 in the first outer surface 602 of the first catheter 600. In some embodiments, the elongate mandrel 500 may be urged toward the first central axis of the first catheter 600 until the elongate mandrel 500 is in contact with the reinforcing braid or coil 608 of the first catheter 600.

Subsequently, the first catheter 600 and the elongate mandrel 500 may be cooled while remaining bound by the first heat shrink material 700 to cure the polymeric material of the first catheter 600 into a desired shape and position (i.e., the U-shaped channel 620). Once cooled, the first heat shrink material 700 and the elongate mandrel 500 may be removed from the first catheter 600 to expose the U-shaped channel 620, as illustrated in cross-section in FIG. 8, in the first outer surface 602. In at least some embodiments where the first mandrel is present within the first lumen 604, the first mandrel may be left in place within the first lumen 604. In some embodiments, the U-shaped channel 620 may be recessed from the first outer surface 602, may extend toward the reinforcing braid or coil 608, and/or may extend to and come into contact with the reinforcing braid or coil 608. A depth of the U-shaped channel 620 into the first outer surface 602 may be controlled by the extent of urging of the elongate mandrel 500 toward the first central axis of the first catheter 600. For example, the more the elongate mandrel 500 is urged toward the first central axis of the first catheter 600, the deeper the U-shaped channel 620 may be, up to the reinforcing braid or coil 608.

Figure 9:
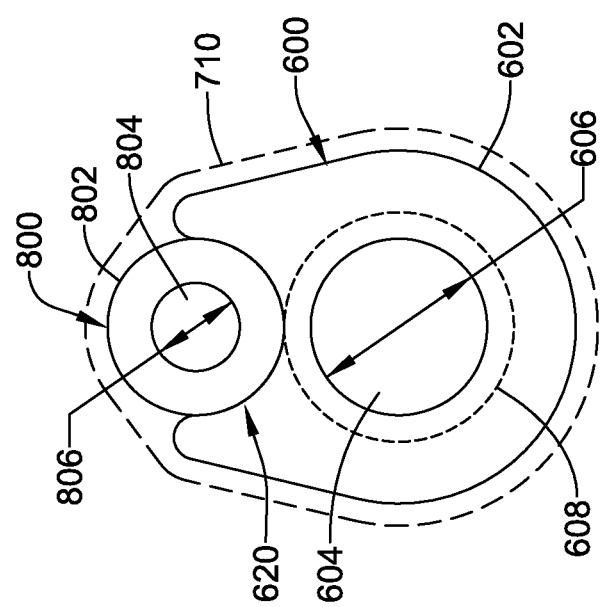

Further as shown in cross-section in FIG. 9, a second catheter 800 may be inserted into the U-shaped channel 620 of the first catheter 600. In some embodiments, the second catheter 800 may include a second lumen 804, a second outer surface 802, a distal end 808, and a proximal end 810/812. In some embodiments, the second lumen 804 may be formed as a central bore having a second inner diameter 806 extending longitudinally therethrough along the second central axis of the second catheter 800. In some embodiments, a wall of the second catheter 800 extending from the second lumen 804 to the second outer surface 802 may define a second wall thickness. In some embodiments, the second wall thickness may be less than the first wall thickness, more than the first wall thickness, or equal to the first wall thickness. In some embodiments, the second inner diameter 806 may be smaller than the first inner diameter 606, larger than the first inner diameter 606, or equal to the first inner diameter 606. In some embodiments, the second catheter 800 may include and/or be formed from a suitable biocompatible polymeric material. Some suitable polymeric materials may be listed below. In some embodiments, the second lumen 804 may include and/or be coated with a suitable friction-reducing material.

In some embodiments, the second catheter 800 may include a second mandrel disposed within the second lumen 804 to maintain the second inner diameter 806 during subsequent heating and/or reflow operations. In some embodiments, the second mandrel may include, may be formed of, or may be coated with a lubricious and/or "non-stick" coating, such as PTFE or other suitable coatings, which may permit easier extraction of the second mandrel from the second lumen 804 of the second catheter 800. Following the subsequent heating and/or reflow operations, the second mandrel may be removed from the second lumen 804 using various suitable methods known in the art. In some embodiments, the second mandrel may further include or be coated with a release agent.

Figure 9A:
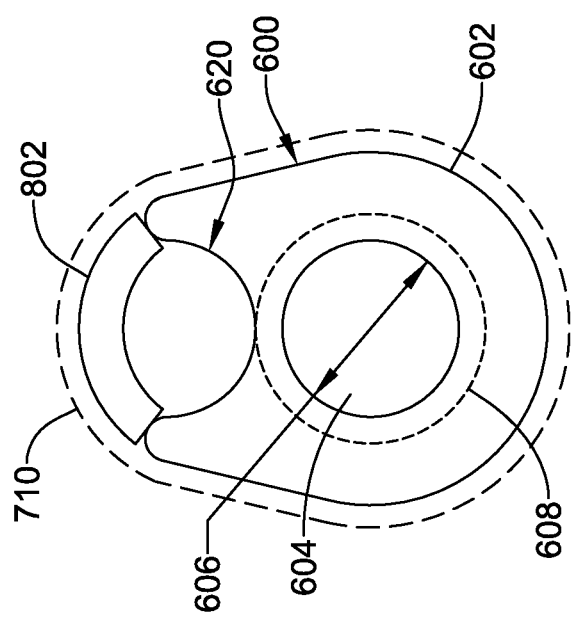
Figure 10:
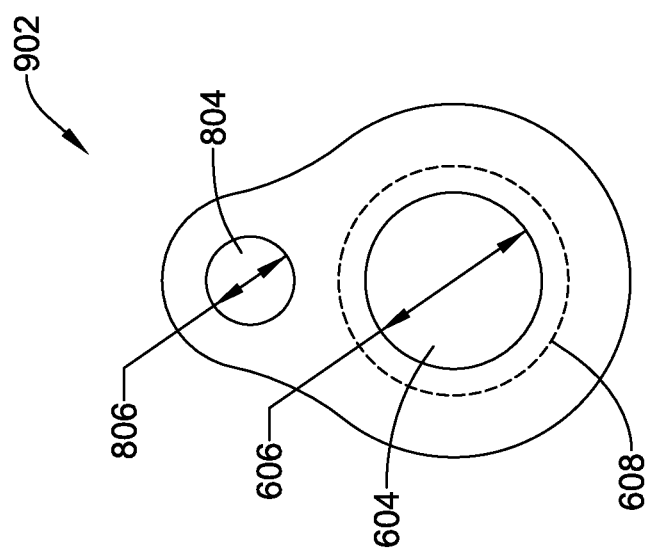
Figure 11:
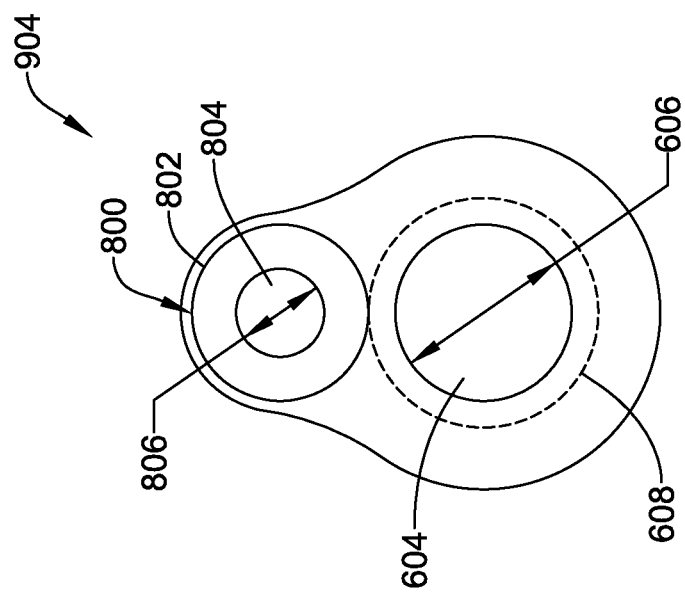
Figure 12:
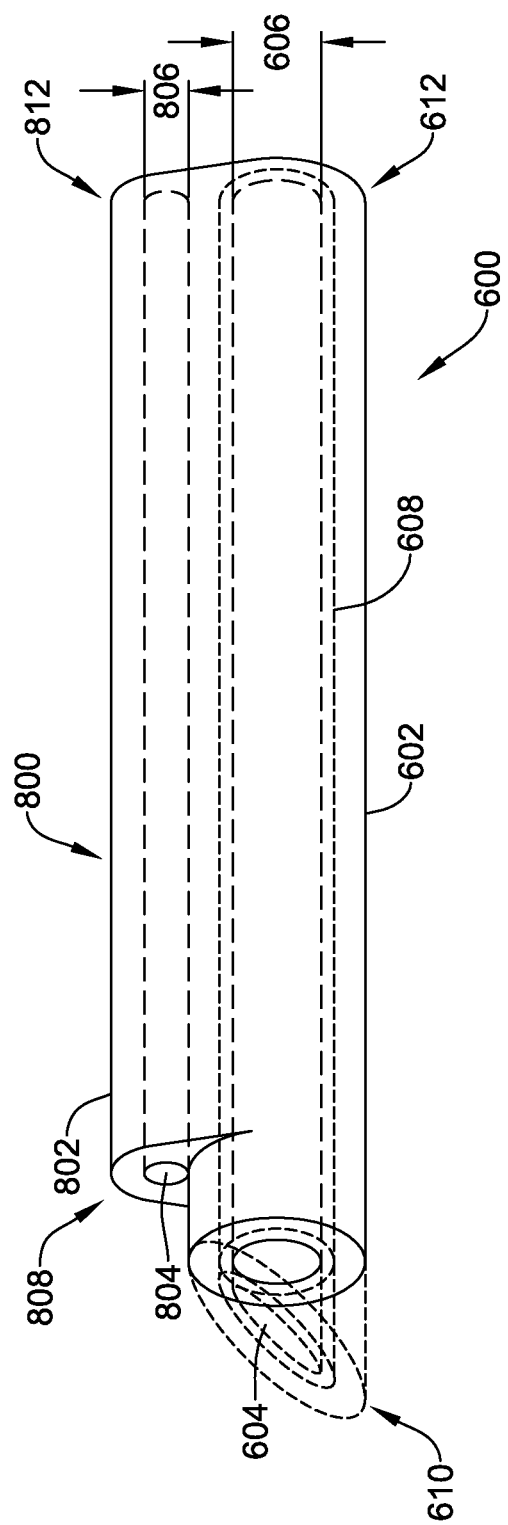
Figure 13:
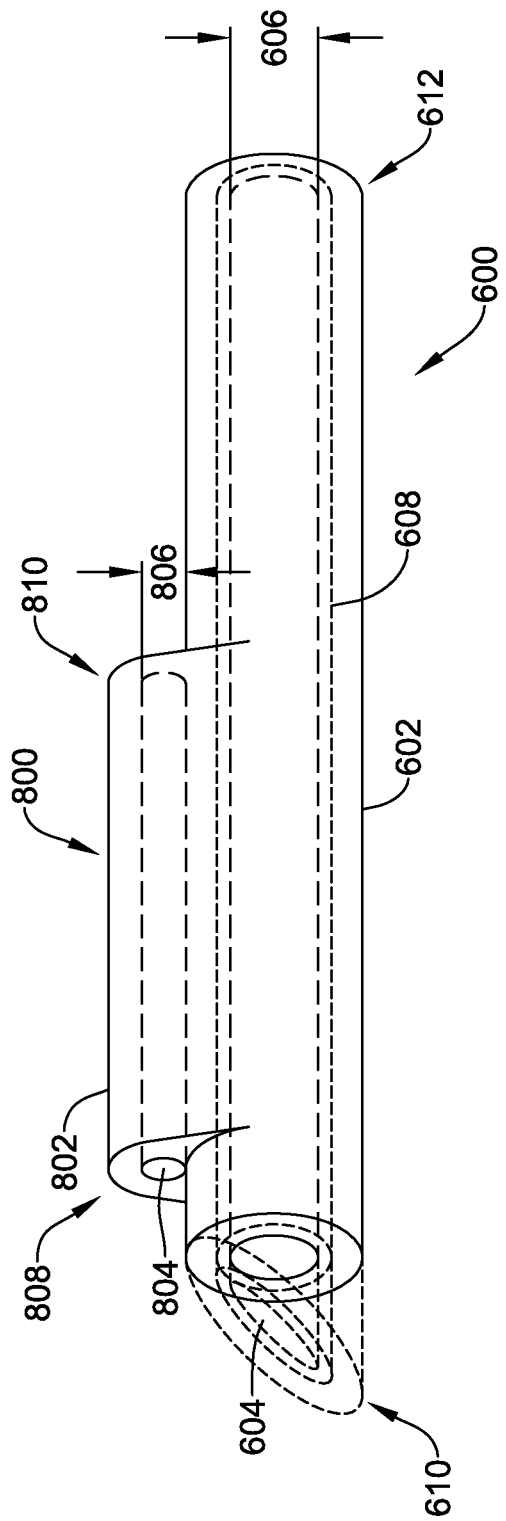

The second catheter 800 may have a variety of configurations and/or arrangements. In some embodiments, a second catheter 800 may be cut, slit, or otherwise reduced in cross-section, and placed against and/or aligned with the U-shaped channel 620, as seen for example, in FIG. 9A, to form a lumen (i.e., the second lumen 804, or its equivalent) therein. In some embodiments, the distal end 808 of the second catheter 800 may be disposed proximal of and/or adjacent to the distal end 610 of the first catheter. In some embodiments, the proximal end 810/812 of the second catheter 800 may be disposed distal of the proximal end 612 of the first catheter 600. For example, in some embodiments, the second catheter 800 may extend proximally to a proximal portion of the first catheter 600. In some embodiments, the second catheter 800 may extend over most or all of the entire length of the first outer surface 602 such that the proximal end 812 of the second catheter 800 may be disposed adjacent to or extending proximal of the proximal end 612 of the first catheter 600, such as in an over-the-wire catheter and as may be seen, for example, in FIG. 12. In some embodiments, the second catheter 800 may extend only along a distal portion of the first outer surface 602 such that the proximal end 810 of a shortened second catheter 800 may be disposed adjacent a distal portion of the first catheter 600, such as in a single operator exchange (SOE) catheter and as may be seen, for example, in FIG. 13. In other words, in some embodiments, the U-shaped channel 620 may extend for less than a full length of the first catheter 600. In some embodiments, a portion of an inner wall surface of the second lumen 804 may be substantially flush with a portion of the first outer surface 602.

It is contemplated that in at least some embodiments, the distal end 808 of the second catheter 800 may be skived, angled, or otherwise slanted relative to a longitudinal axis of the second catheter 800, in a manner similar to the first catheter 600 described above. In some embodiments, the distal end 808 may be arranged at a non-perpendicular angle and/or a non-parallel angle relative to the longitudinal axis of the second catheter 800. In some embodiments, the distal end 808 may be arranged at an angle of about 1 degree to about 89 degrees, about 20 degrees to about 70 degrees, about 30 degrees to about 60 degrees, about 40 degrees to about 50 degrees, or about 45 degrees relative to the longitudinal axis of the second catheter 800.

In some embodiments, the second outer surface 802 of the second catheter 800 may be placed into contact with the reinforcing braid or coil 608 and/or the U-shaped channel 620. The U-shaped channel 620 may help in aligning the second catheter 800 with the first catheter 600 and/or holding the second catheter 800 in place relative to the first catheter 600. In some embodiments, the first central axis of the first catheter 600 may be substantially aligned with the second central axis of the second catheter 800. In some embodiments, the first central axis may be parallel to the second central axis. In some embodiments, the first central axis may be skewed relative to the second central axis, such that if the first central axis and the second central axis are both extended distally, the first central axis and the second central axis may intersect to form an acute angle. The polymeric material of the first catheter 600 displaced by forming the U-shaped channel 620 may eliminate the need to add additional raw material, such as the bead stock element of FIG. 3, for joining, binding, bonding, or otherwise attaching the first catheter 600 to the second catheter 800 during a subsequent reflow process. In some embodiments, the first catheter 600 and the second catheter 800 disposed within the U-shaped channel 620 may be disposed within or placed into a second heat shrink material 710. In some embodiments, the second heat shrink material 710 may be chosen from a variety of heat shrink materials known in the art. For example, in some embodiments, the second heat shrink material 710 may be slidably received over the first catheter 600 and the second catheter 800. In some embodiments, the first catheter 600 may include the first mandrel disposed within the first lumen 604. In some embodiments, the second catheter 800 may include the second mandrel disposed within the second lumen 804. After disposing the first catheter 600 and the second catheter 800 within the second heat shrink material 710, heat may be applied to constrict the heat shrink material around and/or onto the first catheter 600 and the second catheter 800, thereby coupling the first catheter 600 and the second catheter 800 together such that the second catheter 800 is retained within the U-shaped channel 620. In some embodiments, the second heat shrink material 710 may have a designed shrink ratio and wall thickness configured to shrink to a recovered inner diameter or extent when heated. In some embodiments, the recovered inner diameter or extent may be less than a target outer diameter or extent of the first catheter 600 and the second catheter 800 combined so as to create/apply inward force to the reflowing material(s). The wall thickness and/or the differential between the target outer diameter extent and the smaller recovered inner diameter or extent may be used/designed to control and/or generate the desired inward force (i.e., urging).

While being bound by the second heat shrink material 710, the first catheter 600 (including, optionally, the first mandrel disposed within the first lumen 604) and the second catheter 800 (including, optionally, the second mandrel disposed within the second lumen 804) may be heated to cause reflow of one or both of the first catheter 600 and the second catheter 800. Such heating may be performed at a suitable temperature for an appropriate duration based on length, thickness, and/or type of polymeric materials used to fabricate the first catheter 600 and the second catheter 800 to cause the polymeric materials to melt and/or flow together. Upon sufficient heating, one or both of the first catheter 600 and the second catheter 800 may reflow to permanently join, bind, bond, or otherwise attach to each other. A person of ordinary skill in the art may appreciate that any suitable method of joining or bonding may be used including physical coupling, such as mechanical interlocking, and chemical bonding, such as reflowing, hot melting, etc.

In some embodiments, the first catheter 600 and the second catheter 800 may be made of the same thermoplastic polymeric material or different, compatible thermoplastic polymeric materials. Some suitable polymeric materials may be listed below. During the reflow process, the respective thermoplastic polymeric materials of the first catheter 600 and the second catheter 800 may reflow and fuse with each other. The first catheter 600 and the second catheter 800 may be then cooled while being bound by the second heat shrink material 710 to fuse the second catheter 800 with the first catheter 600 to form an integrated multi-lumen catheter 902 with a reduced profile. In some embodiments, the second catheter 800 may be disposed over the first catheter 600 to have a separation between the first lumen 604 and the second lumen 804. The separation may be defined as the sum of: a first wall thickness of the first catheter 600 along a joining line of the first catheter 600 and the second catheter 800, and a second wall thickness of the second catheter 800. In some embodiments, the first wall thickness may be defined as a thickness extending between the reinforcing braid or coil 608 and the first lumen 604 along the joining line. In some embodiments, the second wall thickness may be defined as a thickness extending between the second outer surface 802 and the second lumen 804. The second heat shrink material 710 and (if present) the first mandrel and/or the second mandrel may be then removed from the multi-lumen catheter 902, illustrated in FIG. 10.

In some embodiments, the first catheter 600 may be made of a thermoplastic polymeric material, and the second catheter 800 may be made of a thermoset polymeric material. For example, the second catheter 800 may be made of polyimide or other suitable polymer. During the reflow process, the thermoplastic polymeric material of the first catheter 600 may melt and flow around and encapsulate the second catheter 800 made of a thermoset polymeric material (also referred to as "second thermoset catheter 800"). Since the second thermoset catheter 800 is rigid and may not melt during the reflow process, the second thermoset catheter 800 may have a thinner wall thickness compared to a second catheter 800 formed of a thermoplastic polymeric material. The first catheter 600 and the second thermoset catheter 800 may be cooled while being bound by the second heat shrink material 710 so that the second catheter 800 may be mechanically interlocked with the first catheter 600. Such mechanical interlocking between the first catheter 600 and the second thermoset catheter 800, and the thinner walls of the second thermoset catheter 800 may produce an integrated multi-lumen catheter 904 with a reduced profile. The second heat shrink material 710 may then be removed from the multi-lumen catheter 904, illustrated in FIG. 11.

Such fusing or mechanical interlocking between the first catheter 600 and the second catheter 800 may provide a complementary distributive strength between the first catheter 600 and the second catheter 800. This complementary distributive strength may maintain the integrity of the first lumen 604 of the first catheter 600 and the second lumen 804 of the second catheter 800 during operation and prevent collapse of the first lumen 604 and/or the second lumen 804, even with a reduced wall thickness between them.

Moreover, since the second catheter 800 may be in contact with the reinforcing braid or coil 608 of the first catheter 600 by removing or displacing a portion of the polymeric material between the first catheter 600 and the second catheter 800, the outer profile and/or maximum extent of the multi-lumen catheters 902, 904 may be significantly reduced. Compared to the multi-lumen catheter 400 of FIG. 4, the outer profile of the multi-lumen catheters 902, 904 may be reduced by a part of the wall thickness of the first catheter 600, which was displaced by the elongate mandrel 500 to form the U-shaped channel 620. In some embodiments, the outer profile of the multi-lumen catheters 902, 904 may be reduced by about a distance between the first outer surface 602 and the reinforcing braid or coil 608. The displacement, redistribution, and/or removal of a portion of the polymeric material of the first catheter 600 along a surface joining the first catheter 600 to the second catheter 800 may also improve the flexibility of the multi-lumen catheters 902, 904 compared to the multi-lumen catheter 400.

The materials that can be used for the various components of the first catheter 100, 600, and/or the second catheter 200, 800, etc. (and/or other devices disclosed herein) may include those commonly associated with medical devices. For simplicity purposes, the following discussion makes reference to the first catheter 600 and/or the second catheter 800. However, this is not intended to limit the devices and methods described herein, as the discussion may be applied to other similar tubular members and/or expandable members and/or components of tubular members and/or expandable members disclosed herein.

The first catheter 600 and/or the second catheter 800 may be made from, may be formed of, and/or may include a polymeric material such as polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, other biocompatible polymers, other suitable materials, or mixtures, combinations, copolymers thereof, and the like.

In some embodiments, the elongate mandrel 500 may be made from, may be formed of, and/or may include a metallic material and/or a metallic alloy, such as stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions of the first catheter 600 and/or the second catheter 800 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the first catheter 600 and/or the second catheter 800 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the first catheter 600 and/or the second catheter 800 to achieve the same result.

In some embodiments, a degree of Magnetic Resonance Imaging (MRI) compatibility may be imparted into the first catheter 600 and/or the second catheter 800. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the first catheter 600 and/or the second catheter 800 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A particular cross-sectional shape of the first catheter 600 and/or the second catheter 800 can be any desired shape, for example rounded, oval, rectangular, square, polygonal, and the like, or other such various cross-sectional geometries. The cross-sectional geometries along the length of the first catheter 600 and/or the second catheter 800 can be constant or can vary. For example, the figures depict the first catheter 600 and/or the second catheter 800 as having a generally constant round cross-sectional shape, but it can be appreciated that other cross-sectional shapes or combinations of shapes, while not expressly illustrated, may be utilized without departing from the spirit of the invention.

Additionally, in some embodiments, a coating, for example a lubricious (i.e., hydrophilic, hydrophobic, etc.) or other type of coating may be applied over portions or all of the first catheter 600, the first outer surface 602, the first lumen 604, the second catheter 800, the second outer surface 802, the second lumen 804, the elongate mandrel 500, the outer surface 502, and/or the exterior surface(s) of the multi-lumen catheters 902, 904 discussed above. Hydrophobic coatings such as fluoropolymers, silicones, and the like may provide a dry lubricity which may improve guidewire handling and device exchanges. Lubricious coatings may improve steerability and may improve lesion crossing capability. Suitable lubricious polymers are well known in the art and may include (but are not limited to) hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the elongate mandrel 500 may be coated with polytetrafluroethylene (PTFE).

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A method of making a medical device, the method comprising:
    disposing an elongate mandrel against an outer surface of a first tubular member;
    disposing a first heat shrink material around the first tubular member and the mandrel;
    heating the first tubular member and the elongate mandrel to form a channel along the outer surface of the first tubular member;
    removing the first heat shrink material and the elongate mandrel from the first tubular member;
    disposing a second tubular member within the channel;
    disposing a second heat shrink material around the first tubular member and the second tubular member; and
    heating the first tubular member and the second tubular member to cause reflow between the first tubular member and the second tubular member to form a multi-lumen catheter.

2. The method of claim 1, wherein the first tubular member includes a reinforcing braid or coil.

3. The method of claim 2, wherein when heating the first tubular member and the elongate mandrel, the elongate mandrel is urged into contact with the reinforcing braid or coil.

4. The method of claim 2, wherein when the second tubular member is placed into the channel, an outer surface of the second tubular member is placed into contact with the reinforcing braid or coil.

5. The method of claim 1, wherein the first tubular member, the second tubular member, or both comprise a thermoplastic polymer.

6. The method of claim 5, wherein the first tubular member and the second tubular member comprise the same thermoplastic polymer.

7. The method of claim 1, wherein the second tubular member has a shorter overall length than the first tubular member.

8. The method of claim 1, wherein disposing the second tubular member within the channel includes disposing a distal end of the second tubular member proximal of and adjacent to a distal end of the first tubular member.

9. The method of claim 1, wherein the channel includes a U-shaped channel, and wherein the U-shaped channel extends less than a full length of the first tubular member.

10. A method of making a multi-lumen catheter, the method comprising:
    aligning an elongate mandrel having an outer surface and a central axis extending longitudinally therethrough side-by-side with a first polymeric catheter having a first outer surface and a first lumen having a first inner diameter extending longitudinally therethrough along a first central axis such that the first outer surface contacts the outer surface of the elongate mandrel, and the first central axis is parallel to the central axis of the elongate mandrel;

constricting a first heat shrink material around the first polymeric catheter and the elongate mandrel;

heating the first polymeric catheter and the elongate mandrel while bound by the first heat shrink material and urging the first polymeric catheter and the elongate mandrel toward each other along a plane extending between the first central axis and the central axis of the elongate mandrel to form a U-shaped channel along the first outer surface;

cooling the first polymeric catheter and the elongate mandrel while bound by the first heat shrink material;

removing the first heat shrink material and the elongate mandrel from the first polymeric catheter;

placing a second polymeric catheter having a second outer surface and a second lumen having a second inner diameter smaller than the first inner diameter extending longitudinally therethrough along a second central axis into the U-shaped channel such that the second outer surface is placed into contact with the first polymeric catheter;

constricting a second heat shrink material around the first polymeric catheter and the second polymeric catheter such that the second polymeric catheter is retained within the U-shaped channel;

heating the first polymeric catheter and the second polymeric catheter while bound by the second heat shrink material to cause reflow between the first polymeric catheter and the second polymeric catheter to form the multi-lumen catheter;

cooling the first polymeric catheter and the second polymeric catheter while bound by the second heat shrink material; and removing the second heat shrink material from the multi-lumen catheter.

11. The method of making a multi-lumen catheter of claim 10, wherein the first polymeric catheter includes a reinforcing braid or coil embedded between the first lumen and the first outer surface.

12. The method of making a multi-lumen catheter of claim 11, wherein when urging the first polymeric catheter and the elongate mandrel toward each other, the elongate mandrel is urged into contact with the reinforcing braid or coil.

13. The method of making a multi-lumen catheter of claim 12, wherein when the second polymeric catheter is placed into the U-shaped channel, the second outer surface is placed into contact with the reinforcing braid or coil.

14. The method of making a multi-lumen catheter of claim 10, wherein the first polymeric catheter and the second polymeric catheter each comprise a thermoplastic polymer.

15. The method of making a multi-lumen catheter of claim 14, wherein the first polymeric catheter and the second polymeric catheter each comprise the same thermoplastic polymer.

16. The method of making a multi-lumen catheter of claim 10, wherein the second polymeric catheter has a shorter overall length than the first polymeric catheter.

17. The method of making a multi-lumen catheter of claim 16, wherein placing the second polymeric catheter into the U-shaped channel includes disposing a distal end of the second polymeric catheter proximal of and adjacent to a distal end of the first polymeric catheter.

18. The method of making a multi-lumen catheter of claim 17, wherein a proximal end of the second polymeric catheter is disposed distal of a proximal end of the first polymeric catheter.

19. The method of making a multi-lumen catheter of claim 18, wherein the U-shaped channel extends less than a full length of the first polymeric catheter.

20. A method of making a multi-lumen catheter, the method comprising:

obtaining a first thermoplastic catheter having a first outer surface and a first lumen having a first inner diameter extending longitudinally therethrough along a first central axis;

aligning an elongate mandrel having an outer surface and a central axis extending longitudinally therethrough side-by-side with the first thermoplastic catheter such that the first outer surface contacts the outer surface of the elongate mandrel, and the first central axis is parallel to the central axis of the elongate mandrel;

constricting a first heat shrink material around the first thermoplastic catheter and the elongate mandrel;

heating the first thermoplastic catheter and the elongate mandrel while bound by the first heat shrink material and urging the first thermoplastic catheter and the elongate mandrel toward each other along a plane extending between the first central axis and the central axis of the elongate mandrel to form a U-shaped channel along the first outer surface;

cooling the first thermoplastic catheter and the elongate mandrel while bound by the first heat shrink material;

removing the first heat shrink material and the elongate mandrel from the first thermoplastic catheter;

placing a second thermoset catheter having a second outer surface and a second lumen having a second inner diameter smaller than the first inner diameter extending longitudinally therethrough along a second central axis into the U-shaped channel such that the second outer surface is placed into contact with the first thermoplastic catheter;

constricting a second heat shrink material around the first thermoplastic catheter and the second thermoset catheter such that the second thermoset catheter is retained within the U-shaped channel;

heating the first thermoplastic catheter and the second thermoset catheter while bound by the second heat shrink material to cause the first thermoplastic catheter to reflow around and encapsulate the second thermoset catheter to form the multi-lumen catheter;

cooling the first thermoplastic catheter and the second thermoset catheter while bound by the second heat shrink material; and removing the second heat shrink material from the multi-lumen catheter.

* * * * *